United States Patent [19]
Chung

[11] Patent Number: 5,665,913
[45] Date of Patent: Sep. 9, 1997

[54] METHOD AND APPARATUS FOR EVALUATION AND INSPECTION OF COMPOSITE-REPAIRED STRUCTURES

[75] Inventor: J. H. Chung, Rockwall, Tex.

[73] Assignee: E-Systems, Inc., Dallas, Tex.

[21] Appl. No.: 612,421

[22] Filed: Mar. 7, 1996

[51] Int. Cl.$^6$ ............................................. G01N 29/06
[52] U.S. Cl. ........................................ 73/583; 73/597
[58] Field of Search ............................ 73/597, 598, 599, 73/600, 602, 620, 627, 583; 364/507, 508

[56] References Cited

U.S. PATENT DOCUMENTS

| | | | |
|---|---|---|---|
| 3,341,774 | 9/1967 | Dyben | 324/663 |
| 4,301,684 | 11/1981 | Thompson et al. | 73/602 |
| 4,387,601 | 6/1983 | Azegami | 73/724 |
| 4,667,149 | 5/1987 | Cohen et al. | 324/715 |
| 4,887,025 | 12/1989 | Re Fiorentin et al. | 324/693 |
| 4,956,999 | 9/1990 | Bohannan et al. | 73/587 |
| 4,983,034 | 1/1991 | Spillman, Jr. | 356/32 |
| 5,093,626 | 3/1992 | Baer et al. | 324/671 |
| 5,113,079 | 5/1992 | Matulka | 250/550 |
| 5,195,046 | 3/1993 | Gerardi et al. | 364/506 |
| 5,202,641 | 4/1993 | Unvala | 324/715 |
| 5,374,011 | 12/1994 | Lazarus et al. | 244/75 R |

*Primary Examiner*—Hezron E. Williams
*Assistant Examiner*—Rose M. Miller
*Attorney, Agent, or Firm*—Harold E. Meier

[57] ABSTRACT

A method and apparatus for evaluation and inspection of a composite-repaired structure generates a frequency-varying electrical signal to test and evaluate the composite-repaired area. The electrical signal is converted into a mechanical signal and transmitted through the composite-repaired area of the structure. The transmitted mechanical signal is received and converted into an electrical signal for processing. The processed signal is compared with a baseline reference signal to determine whether the composite-repaired area is damaged or undamaged. The baseline reference signal is obtained at the time of the composite repair of the structure.

6 Claims, 5 Drawing Sheets

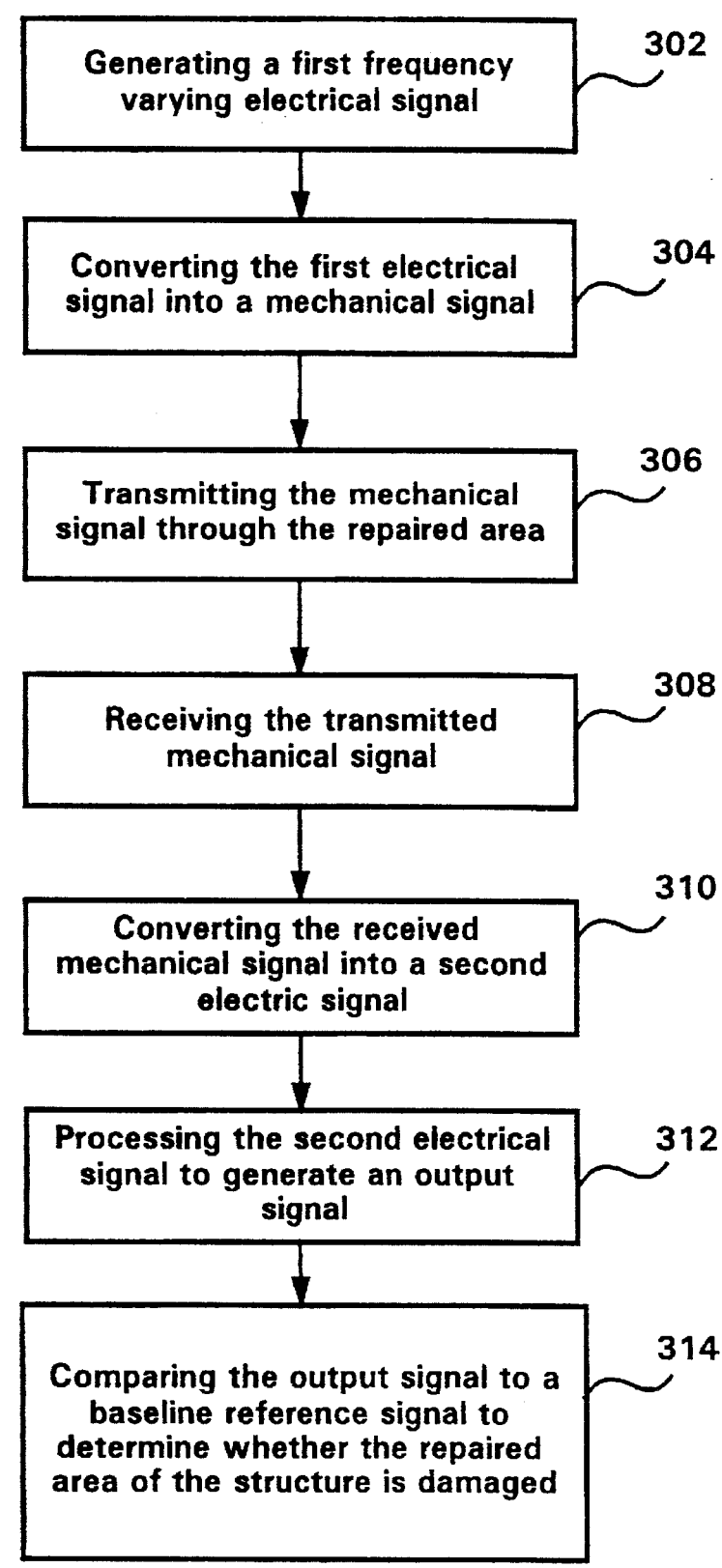

METHOD AND APPARATUS FOR EVALUATION AND INSPECTION OF COMPOSITE-REPAIRED STRUCTURES

TECHNICAL FIELD

The present invention relates to an apparatus and method for evaluation and inspection of structures and, in particular, to an apparatus and method for non-destructive evaluation and inspection of composite-repaired metal structures.

BACKGROUND OF THE INVENTION

In the aerospace industry, as well as other industries, utilizing critically important structural members, repair of damaged structural members is increasingly being performed using composite repair. Composite repair refers to the repair of a damaged structure (e.g., an aluminum aircraft wing panel having a damaged area) by adhesively bonding a composite material, such as a multiple ply composite material, to the damaged structure.

After the structure has been composite-repaired and is put back into service, the integrity of the composite-repaired structure must generally be monitored. Periodically, these composite-repaired structures undergo non-destructive evaluation and inspection (NDE/I) to ensure the composite repair is not damaged or otherwise failing.

Conventional NDE/I techniques utilize eddy-current, ultrasound, thermal imaging, laser, X-ray, etc. All of these techniques require substantial accessibility to the structure to be evaluated and inspected. In aircraft structure evaluation and inspection, for example, performance of conventional NDE/I requires disassembly of the aircraft structure(s) to gain access to the inspection article. In some cases of composite-repaired structural inspection, such as inspection of a C-130 outer wing fuel tank, it requires upwards of 1300 man-hours to disassemble the aircraft structure to gain access to the inspection article for conventional NDE/I.

Accordingly, there exists a need for an apparatus and method for non-destructive evaluation and inspection of a repaired structure that reduces or eliminates the need for substantial accessibility in order to monitor, evaluate and/or inspect the repaired structure. Further, there exists a need for an apparatus and method for NDE/I of intact composite-repaired structures, thus reducing or eliminating the need for disassembly of the composite-repaired structure or article from the overall structure.

SUMMARY OF THE INVENTION

According to the present invention, there is provided an apparatus and method for non-destructive evaluation and inspection of a repaired area of a structure. The present invention includes a signal generator for generating a first electrical signal. A transducer coupled to the signal generator and to the structure converts the first electrical signal into a mechanical signal for transmission through the repaired area of the structure. Another transducer coupled to the structure receives and converts the mechanical signal into a second electrical signal. The apparatus further includes a signal processor coupled to the second transducer for generating, in response to the second electrical signal, an output signal indicative of the present condition of the repaired area of the structure. The output signal is then used for comparison to a baseline reference signal to determine whether the repaired area of the structure is damaged. The baseline reference signal is generated after repair of the structure is accomplished.

In an alternative embodiment of the present invention, the signal processor includes an impedance analyzer for measuring the impedance response of the repaired area in relation to the frequency of the first electrical signal generated by the signal generator. The impedance response measured at the time of testing is compared with the impedance response measured at the time of repair of the structure (undamaged condition) to determine if the repaired area is damaged.

DESCRIPTION OF THE DRAWINGS

For a more complete understanding of the present invention and the advantages thereof, reference is made to the following detailed description taken in conjunction with the accompanying drawings wherein:

FIG. 5 illustrates a method of non-destructive evaluation and testing of a repaired area of a structure in accordance with the present invention.

DETAILED DESCRIPTION

Figure 1:
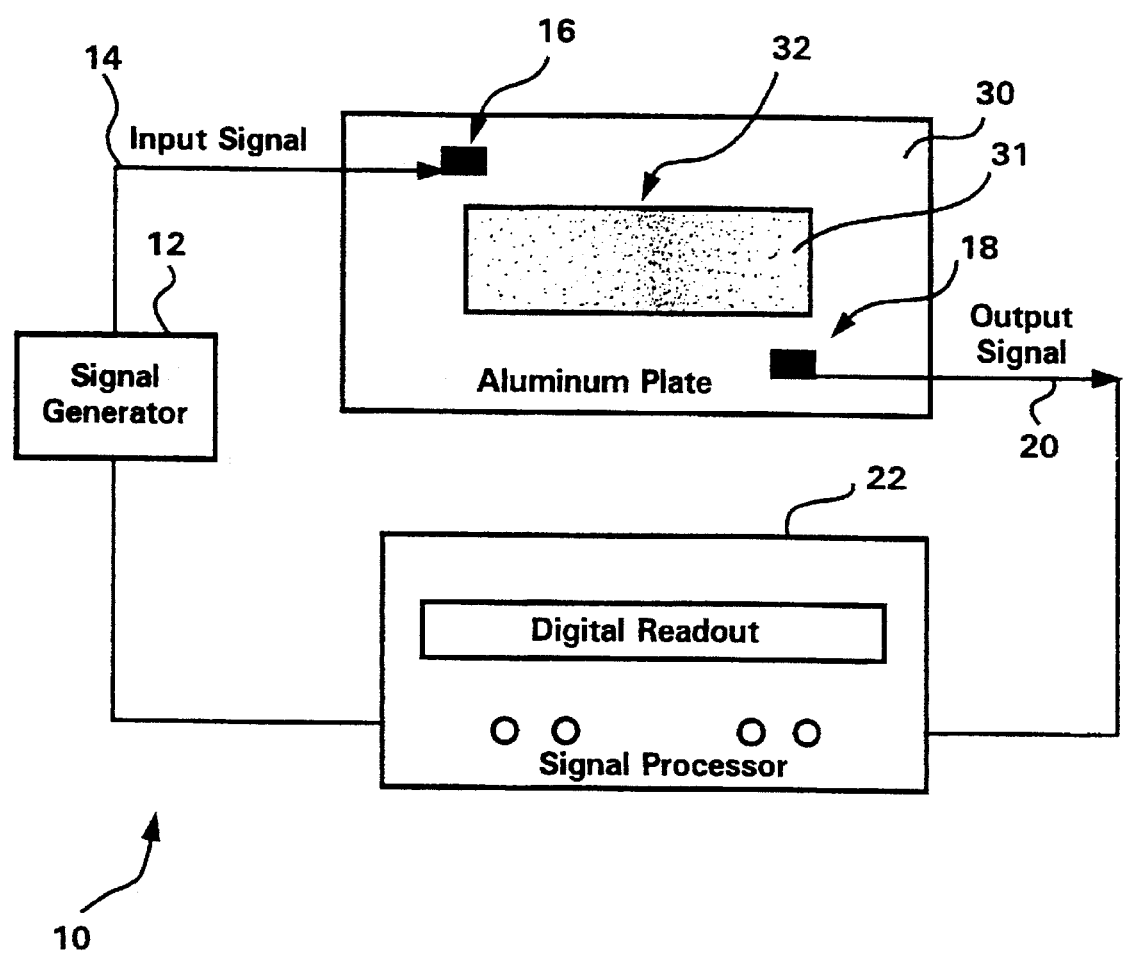
FIG. 1 illustrates a block diagram of an apparatus for non-destructive evaluation and inspection of a repaired structure in accordance with the present invention.

With reference to the drawings, like reference characters designate like or similar parts throughout the drawings.

With reference to FIG. 1, there is shown a non-destructive evaluation and inspection tester 10 in accordance with the present invention. The tester 10 includes a signal generator 12, a first transducer 16, a second transducer 18 and a signal processor 22. The signal generator 12 generates and outputs a frequency-varying test electrical signal 14 having voltage= v*sin(wt) and current=i*sin(wt+q), where v and i are the amplitude of the voltage and current, respectively. In the preferred embodiment, the signal generator 12 is a sine wave generator and the test signal 14 varies in frequency over time, such as a sine sweep over a predetermined frequency range.

Also in FIG. 1, there is shown a composite-repaired structure 30 having a composite repair doubler 32 including a composite-repaired area 31. Typically, the structure 30 is a metal structure such as an aluminum plate. Generally, the composite repair doubler 32 is used to repair a damaged area of the structure 30 by having the composite repair doubler adhesively bonded onto the structure 30 to repair the damaged area. The composite repair doubler 32 covers the composite-repaired area 31. It is the integrity of the composite repair doubler 32 or area 31 that is tested by the present invention.

The first transducer 16 is coupled to, or installed onto, the structure 30 near the composite repair doubler 32, as shown. The first transducer 16 is also electrically coupled to the signal generator 12 and receives the signal 14. The first transducer 16 converts the signal 14 into a mechanical signal and transmits the mechanical signal into the composite repair area 31 and through both the structure 30 and composite repair doubler 32.

The second transducer 18 is also coupled to, or installed onto, the structure near the composite repair doubler 32, as shown. As will be appreciated, the transducers 16, 18 can be located in any configuration, with a preferred configuration such that an imaginary line drawn between the two transducers 16, 18 intersects a point on the composite repair doubler 32, i.e. in the area 31. In the preferred embodiment, the transducers 16, 18 are positioned diagonal to the corners of the doubler 32, as shown, such that the imaginary line drawn between the traducers 16, 18 substantially intersects with the central region of the composite repair doubler 32 (area 31).

The mechanical signal produced by the transducer 16 travels through both the structure 30 and the composite repair doubler 32 (area 31) and is received by the transducer 18. The transducer 18 converts the received mechanical signal into an electrical signal and outputs a response electrical signal 20. In the preferred embodiment, the transducers 16, 18 are piezoelectric transducers (PZT) whereby the first transducer 16 is a signal transmitter PZT and the second transducer 18 is a sensor PZT.

After output from the second transducer 18, the signal 20 is input to the signal processor 22 for processing to generate an output signal indicative of the present condition of the composite-repaired structure 30. Damage detection of the composite-repaired structure 30 (i.e. damage of the composite repair doubler 32 in the form of delamination, disbond, crack propagation, etc.; and increased damage to the structure 30 such as crack propagation, etc.) is accomplished by comparing the present output signal from the transducer 18 to a baseline reference signal generated at the time of composite repair and stored in the signal processor 22 for subsequent comparison.

As will be understood, the baseline reference signal(s), representing the undamaged condition of the composite-repaired structure 30, is generated at the time of the composite repair of the structure 30. The baseline reference signal(s) is then stored for later use when the composite-repaired structure 30 is tested and inspected to determine the integrity (damaged or undamaged) of the repair after the composite-repaired structure 30 has been in use for some period of time.

Figure 2:
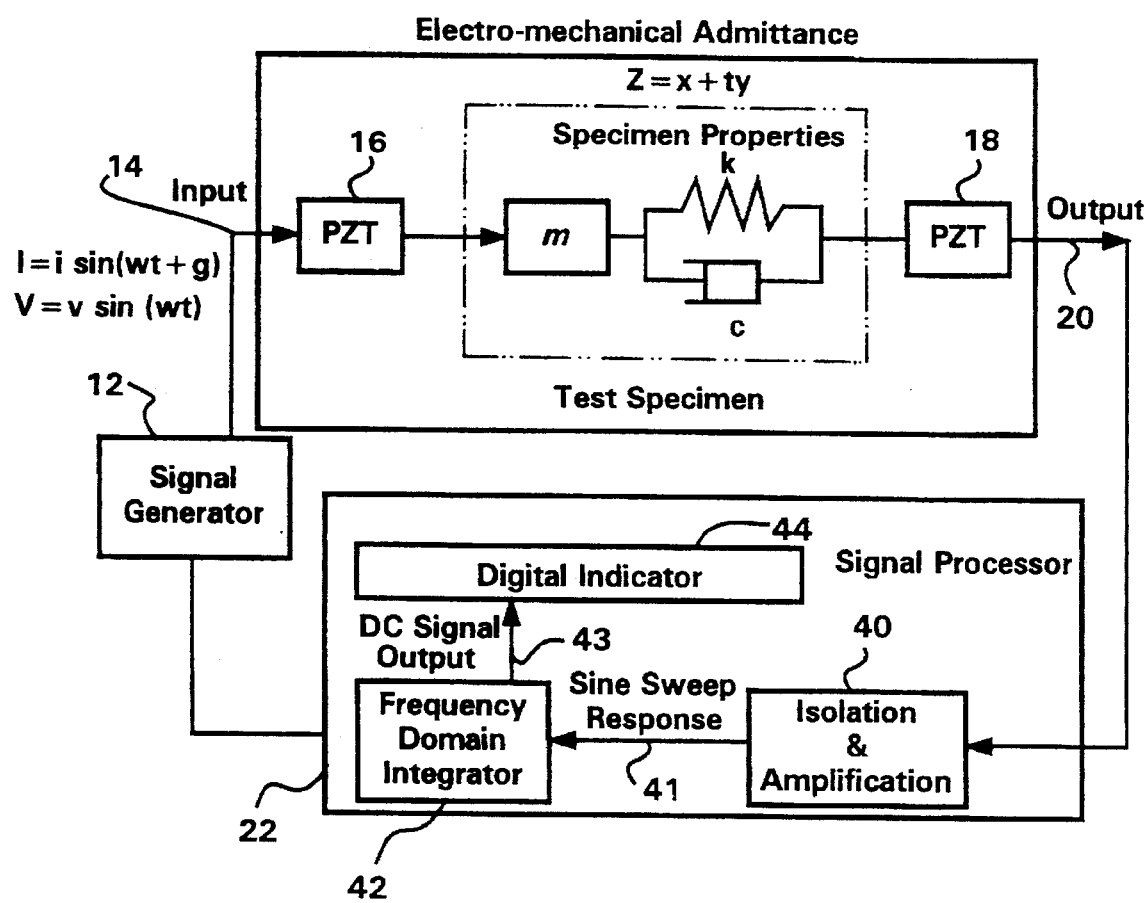
FIG. 2 illustrates an electro-mechanical diagram of the present invention and illustrates a more detailed block diagram of a signal processor used in accordance with the present invention.

Now referring to FIG. 2, there is illustrated an electromechanical diagram of the present invention and a more detailed block diagram of the signal processor 22. The signal processor 22 includes an isolation filter and amplifier 40, a frequency domain integrator 42, and a digital indicator 44. The response electrical signal 20 (the current test signal) output from the second transducer 18 is input to the filter and amplifier 40. The filter and amplifier 40 filters out any signals having frequencies outside the range of frequencies of the test electrical signal 14 generated by the signal generator 12, and further amplifies the filtered signal. The filtered signal, referred to as the sine sweep response 41, is input to the frequency domain integrator 42. The frequency domain integrator 42 generates and outputs a DC signal 43 in response to the sine sweep response 41. The digital indicator 44 receives the DC signal 43 and provides a display (or value) indicative of the present condition of the composite-repaired structure 30. The display is thereafter read or stored by the user for comparison with the baseline reference signal(s).

As illustrated in FIG. 2, the composite repair doubler 32 possesses particular electro-mechanical admittance and/or impedance characteristics. These characteristics are determined by the physical and/or chemical properties of the materials of the composite repair doubler 32. These properties include inertia, spring and viscous damping designated by coefficients m, k and c, respectively, with the mechanical properties analogous to the electrical properties of inductance, capacitance and resistance. A change in the physical and/or chemical characteristics of the composite repair doubler 32 causes a corresponding change in the coefficients m, k or c. It is this change (difference measured at two different times) that is used to detect the presence of a damaged condition (delamination, disbond, crack propagation, etc.) of the composite repair doubler 32.

Figure 3:
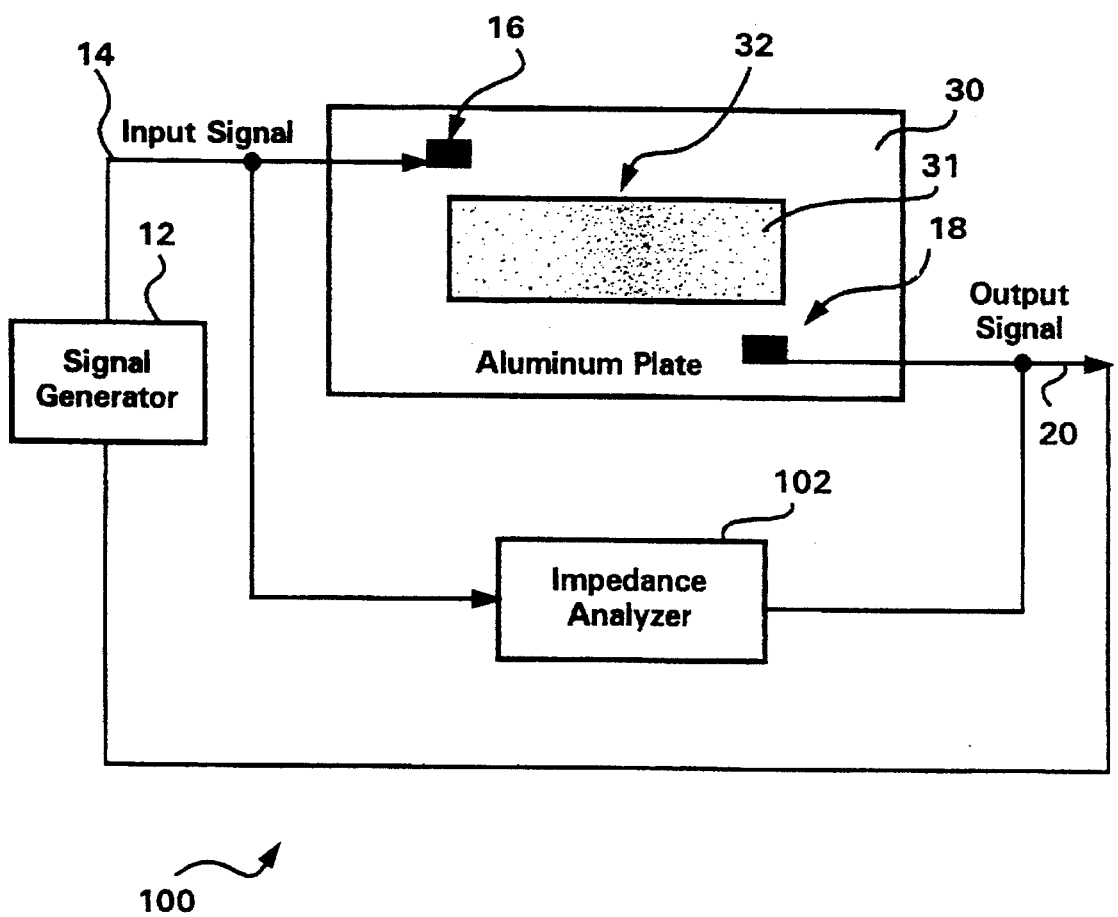
FIG. 3 shows an alternative embodiment of the present invention illustrating the use of an impedance analyzer.

Now referring to FIG. 3, there is shown an alternative embodiment of a tester 100 in accordance with the present invention. In replacement of the signal processor 22 in the tester 10, an impedance analyzer 102 is coupled to the test electrical signal 14 and the response electrical signal 20. The impedance analyzer 102 measures the impedance and/or admittance from the first transducer 16 to the second transducer 18. As will be understood, a damaged condition in the composite repair doubler 32 will result in an impedance response different from the impedance response (baseline reference signal) generated from an undamaged composite repair doubler 32. Preferably, the impedance analyzer 102 is a Hewlett-Packard HP 4194A impedance analyzer capable of providing impedance signal response (magnitude and phase) graphs or plots in relation to frequency (of the test electrical signal 14). As will be appreciated, any measuring equipment, and the like, capable of measuring any change(s) in the properties of the composite repair doubler 32 detected in response to the signal(s) passing through the composite repair doubler 32 may be used.

The following provides an example of the detection of a damaged composite repair doubler 32 in accordance with the present invention: A 14-ply B/Epoxy composite repair doubler 32 (7.5 inch length, 2.5 inch width, 0.1 inch thickness) was applied to an aluminum plate specimen 30. During application, a thin metallic shim (1.25 inch length, 0.5 inch width, 0.05 inch thickness) was inserted between the composite repair doubler 32 and the aluminum plate specimen 30.

After the composite repair doubler 32 was cured, the test specimen was tested using the tester 10 in accordance with the test configuration shown in FIG. 1. The digital readout from the signal processor 22 provided an output signal of "68". Further, the test specimen was tested using the tester 100 in accordance with the test configuration shown in FIG. 3 whereby impedance-vs-frequency plots or graphs were obtained from the impedance analyzer 102.

After the baseline signals from the above testing of the undamaged composite doubler 32 were generated, the thin metallic shim was removed from the composite repair doubler 32 to provide a damaged condition (disbond) for the composite repair doubler 32. Using the test configuration shown in FIG. 1, the output signal from the tester 10 provided a reading of "92". An output signal of "68" was generated by the tester 10 for an undamaged condition and an output signal of "92" for a damaged condition.

Figure 4A:
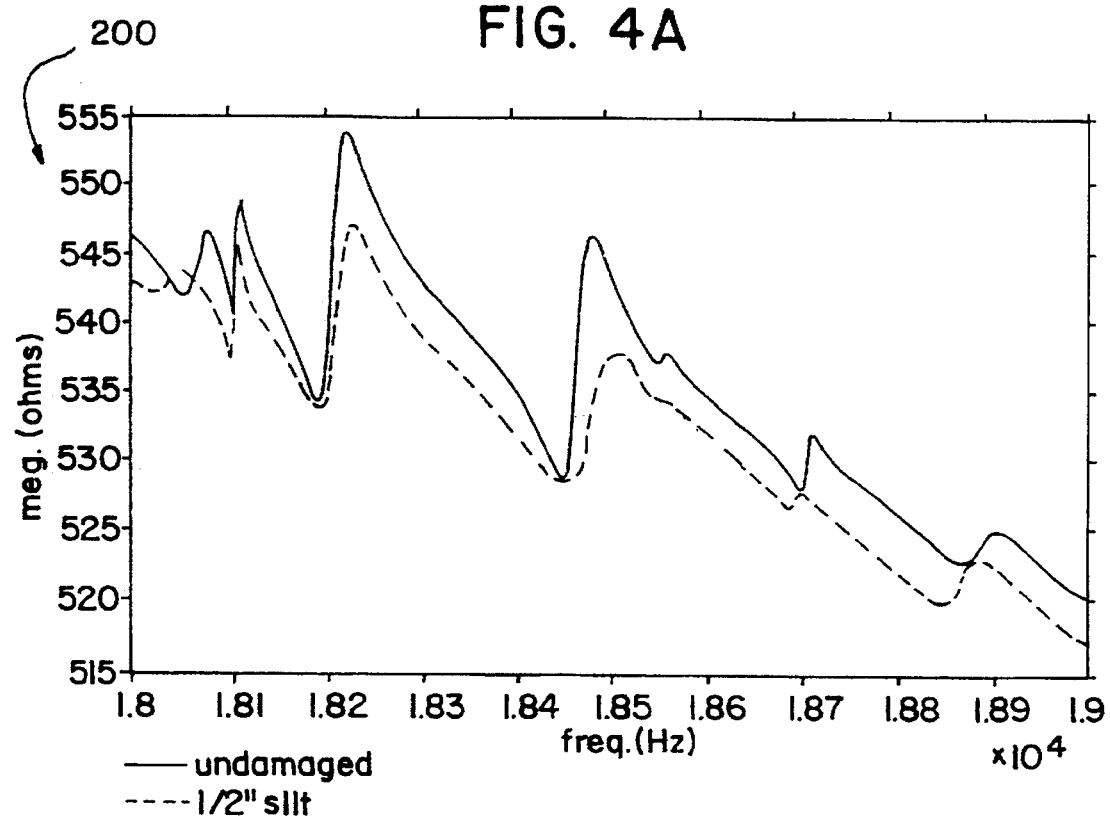
FIGS. 4A and 4B illustrate two impedance-vs-frequency signal plots for an undamaged repaired area and a corresponding damaged repaired area.
Figure 4B:
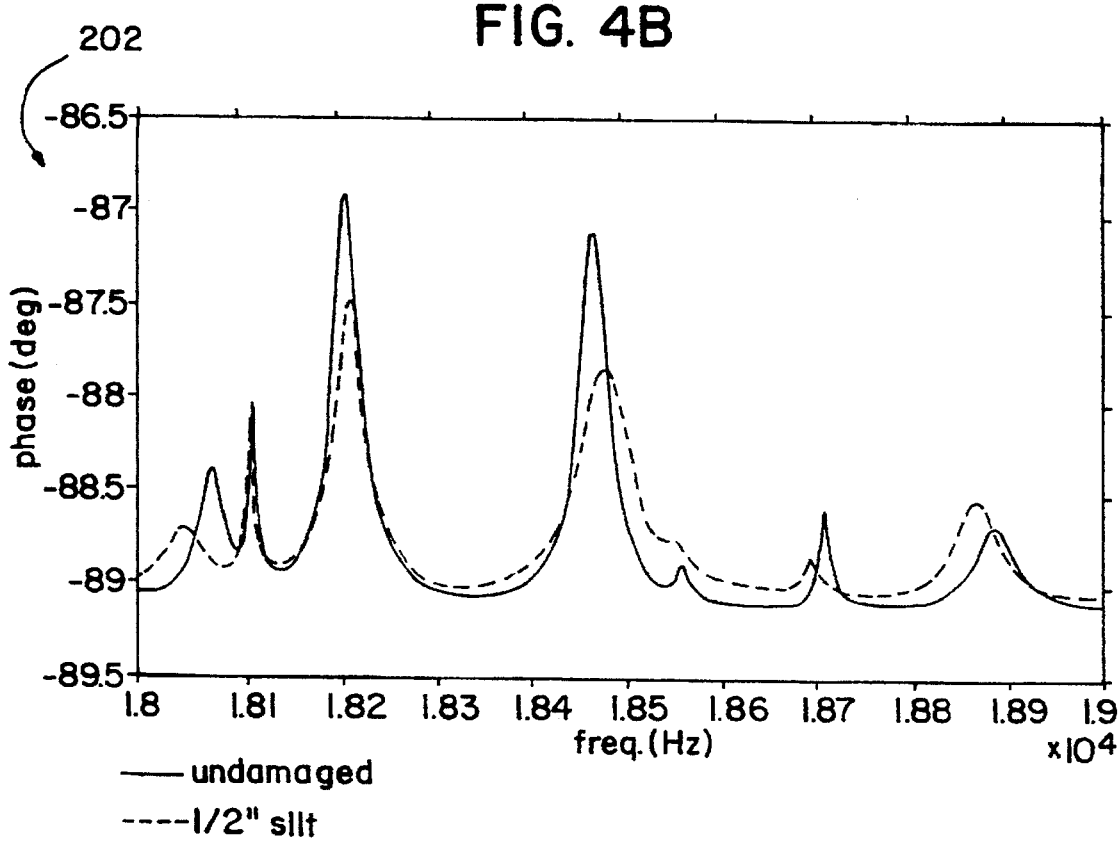

Likewise, impedance-vs-frequency plots or graphs were generated from the impedance analyzer 102 for the damaged condition. The graphs generated from the undamaged and damaged composite repair doubler were overlayed and the resulting graphs 200, 202 are shown in FIGS. 4A and 4B. The solid line represents measurements for the undamaged condition and the dotted line represents measurements for the damaged condition. Clearly, there is detected a distinct difference between the undamaged and damaged conditions.

Now referring to FIG. 5, there is shown a method 300 for non-destructive evaluation and testing of a repaired area of a structure in accordance with the present invention. At a step 302, the signal generator 12 generates the test electrical signal 14 for input to the first transducer 16. In the preferred embodiment, the frequency of the test electrical signal 14 varies according to a desired pattern (e.g. frequency sweeping from 18 KHz to 19 KHz over a time period T). As will be appreciated, the signal 14 may have a single frequency or a range of frequencies. At a step 304, the electrical signal 14 is converted into a mechanical signal. The mechanical signal is transmitted through the composite-repaired doubler 32 (i.e. the repaired area 31) at a step 306.

After transmission through the repaired area 31, the mechanical signal is received by the second transducer 18 at a step 308. At a step 310, the received mechanical signal is converted into the response electrical signal 20. The signal 20 is processed to generate a display signal at a step 312. At a step 314, the output signal is compared to a baseline reference signal to determine whether the composite-repaired doubler (the repaired area 31) of the structure 30 is damaged. As will be appreciated, an alternative embodiment of the method 300 includes repeating the steps 302 through 312 after the structure 30 is repaired with the composite repair doubler 32. Performance of these steps after repair of the structure will generate the baseline reference signal that is used, at step 314, for comparison to the output signal to determine if a damaged condition is present.

Although several embodiments of the present invention has been described in the foregoing detailed description and illustrated in the accompanying drawings, it will be understood by those skilled in the art that the invention is not limited to the embodiments disclosed but is capable of numerous rearrangements, substitutions and modifications without departing from the spirit of the invention.

What is claimed is:

1. An apparatus for testing and inspection of a composite-repaired area of a structure, comprising:

a signal generator generating a test signal;

means coupled to the structure and receiving the test signal from the signal generator for converting the test signal to a mechanical signal for transmission through a portion of the composite-repaired area of the structure;

means coupled to the structure for receiving the mechanical signal transmitted through the structure and converting the received mechanical signal into a response signal; and a signal processor coupled to the means for receiving includes a filter and an integrator, said filter masks from the responsive signal a range of signals outside the frequency of the test signal generating a sine sweep response, said integrator integrating the sine sweep and outputs a display signal indicative of the present condition of the composite-repaired area of the structure for comparison to a baseline reference signal representing a previously repaired condition of the composite-repaired area.

2. The apparatus in accordance with claim 1 wherein the means for generating the display signal comprises an impedance analyzer coupled across the area of the structure for measuring the impedance of the area and for generating an impedance versus frequency signal as the display signal.

3. An apparatus for testing of a composite-repaired area of a structure, comprising:

a signal generator generating a first electrical signal having a frequency;

a first transducer coupled to the structure and coupled to the signal generator for converting the first electrical signal into a mechanical signal for transmission through the composite-repaired area of the structure;

a second transducer coupled to the structure for receiving and converting the mechanical signal into a second electrical signal; and a signal processor coupled to the second transducer, said signal processor includes a filter and frequency domain integrator, said filter masks from the second electrical signal a range of signals outside the frequency of the first electrical signal generating a sine sweep response, said frequency domain integrator integrating the sine sweep response to generate an output signal indicative of the present condition of the composite-repaired area of the structure for comparison to a baseline reference signal representing a previously repaired condition of the composite-repaired area.

4. An apparatus for testing and inspection of a composite-repaired area of a structure, comprising:

a signal generator generating a test signal;

means coupled to the structure and receiving the test signal from the signal generator for converting the test signal to a mechanical signal for transmission through a portion of the composite-repaired area of the structure;

means coupled to the structure for receiving the mechanical signal transmitted through the structure and converting the received mechanical signal into a response signal; and an impedance analyzer coupled to the response signal and the test signal for measuring the impedance of the area and for generating an impedance versus frequency signal as a display signal.

5. The apparatus in accordance with claim 4 wherein the test signal generated by the signal generator comprises a frequency-varying signal.

6. A method for evaluation and testing of a composite-repaired area of a structure, comprising the steps of:

determining a baseline reference signal from the composite-repaired area of the structure;

determining an output signal from the composite-repaired area of the structure, said output signal measured at a time after the step of determining the baseline reference; and comparing the baseline reference signal and the output signal to ascertain the condition of the composite-repaired area of the structure;

wherein the steps of determining the baseline reference signal and the output signal each includes:

transmitting a signal through the composite-repaired area of the structure, further including the steps of:
generating a first frequency-varying electrical signal;
convening the first electrical signal into a mechanical signal;
transmitting, at a first location on the structure, the mechanical signal through a
portion of the composite-repaired area of the structure;

receiving the transmitted signal, further including the steps of:
receiving, at second location on the structure, the mechanical signal;
converting the received mechanical signal into a second electrical signal; and
processing the second electrical signal to generate the baseline reference signal or the output signal wherein the step of processing includes the steps of:

filtering out from the second electrical signal a range of signals outside the frequency of the transmitted signal to generate a sine sweep response; and integrating the sine sweep response to generate either the baseline reference signal or the output signal.

* * * * *